US006444787B1

(12) United States Patent
Pincus

(10) Patent No.: US 6,444,787 B1
(45) Date of Patent: Sep. 3, 2002

(54) METHOD OF ISOLATING A PEPTIDE WHICH IMMUNOLOGICALLY MIMICS MICROBIAL CARBOHYDRATES INCLUDING GROUP B STREPTOCOCCAL CARBOHYDRATES AND THE USE THEREOF IN A VACCINE

(75) Inventor: Seth H. Pincus, Bozman, MT (US)

(73) Assignee: Research Development Institute, Inc., Bozeman, MT (US)

( * ) Notice: Subject to any disclaimer, the term of this patent is extended or adjusted under 35 U.S.C. 154(b) by 0 days.

(21) Appl. No.: 09/222,779

(22) Filed: Dec. 30, 1998

Related U.S. Application Data

(60) Provisional application No. 60/070,118, filed on Dec. 31, 1997.

(51) Int. Cl.$^7$ .......................... A61K 38/04; C12P 19/00
(52) U.S. Cl. ...................... 530/327; 435/72; 435/235.1; 435/243; 435/172.3; 435/DIG. 22; 435/DIG. 35
(58) Field of Search ................. 530/327, 806, 530/808, 825; 435/72, 82, 101, 172.1, 235.1, 340, 243, 253.4, 885, 965, 172.3, DIG. 22, DIG. 3, DIG. 4, DIG. 15, DIG. 34, DIG. 35; 430/200

(56) References Cited

U.S. PATENT DOCUMENTS 5,648,241 A * 7/1997 Mitchel et al. ............. 435/69.3
5,846,547 A * 12/1998 Cleary ...................... 424/244.1

FOREIGN PATENT DOCUMENTS

| WO | WO 91/04049 | 4/1991 |
| WO | WO 94/26886 | 11/1994 |
| WO | WO 97/46582 | 12/1997 |

OTHER PUBLICATIONS

Ashley Publications Ltd., Peptide Mimetics of Carbohydrate Epitopes: Strategies to Block Hyperacute Rejection of Porcine Xenografts, Expert Opinion on Therapeutic Patents, vol. 7, No. 11, Nov. 1997, pp. 1345–1350.

Bonin, P. et al., A Peptide Inhibitor of Cholesteryl Ester Transfer Protein Identified by Screening a Bacteriophage Display Library, Journal of Peptide Research, 1998, vol. 51, pp. 216–225.

Guttormsen, H. et al., Immunologic Memory Induced by a Glycoconjugate Vaccine in a Murine Adoptive Lymphocyte Transfer Model, Infection and Immunity, May 1998, vol. 66, No. 5, pp. 2026–2032.

Hordnes, K. et al., Nasal Immunization with Group B Streptococci Can Induce High Levels of Specific IgA Antibodies in Cervicovaginal Secretions of Mice, Vaccine, vol. 15, No. 11, 1997, pp. 1244–1251.

Kieber–Emmons, T., Peptide Mimotopes of Carbohydrate Antigens, Immunologic Research, 1998, vol. 17/1&2, pp. 95–108.

Magliani, W. et al., Neonatal Mouse Immunity Against Group B Streptococcal Infection by Maternal Vaccination with Recombinant Anti–Idiotypes, Nature Medicine, vol. 4, No. 6, Jun. 1998, pp. 705–709.

Phalipon, A. et al., Induction of Anti–Carbohydrate Antibodies by Phage Library–Selected Peptide Mimics, Eur. J. Immunol., 1997, vol. 27, pp. 2620–2625.

Wessels, M. et al., Structural Properties of Group B Streptococcal Type III Polysaccharide Conjugate Vaccines That Influence Immunogenicity and Efficacy, Infection and Immunity, May 1998, vol. 66, No. 5, pp. 2186–2192.

Wong, D.W.S. et al., Identifying Peptide Ligands for Barley α–Amylase 1 Using Combinatorial Phage Display Libraries, J. Agric. Food Chem., 1998, vol. 46, pp. 3852–3857.

Young, A. et al., The Three–Dimensional Structures of a Polysaccharide Binding Antibody to Cryptococcus Neoformans and its Complex with a Peptide from a Phage Display Library: Implications for the Identification of Peptide Mimotopes, J. Mol. Biol., 1997, vol. 274, pp. 622–634.

David, S., et al., Isolation and partial characterization of human antibody fragments specific for group B Streptococcal (GBS) type III capsular polysaccharide isolated by phage display, Immunotechnology, 1996, vol. 2, No. 4, p. 285.

Feldman, R.G., et al., The Group B Streptococcal Capsular Carbohydrate: Immune Response and Molecular Mimicry, Advances in Experimental Medicine and Biology, 1998, vol. 435, pp. 261–269.

Harris, S.L., et al., Exploring the basis of peptide–carbohydrate crossreactivity: Evidence for discrimination by peptides between closely related anti–carbohydrate antibodies, Proc. Natl. Acad. Sci. USA, 1997, vol. 94, No. 6, pp. 2454–2459.

PCT International Search Report of PCT/US 98/27931.

Pincus, S. H., et al., Peptides That Mimic the Group B Streptococcal Type III Capsular Polysaccharide Antigen, The Journal of Immunology, 1998, vol. 160, No. 1, pp. 293–298.

(List continued on next page.)

Primary Examiner—Padmashri Ponnaluri
(74) Attorney, Agent, or Firm—Morgan, Lewis & Bockius LLP

(57) ABSTRACT

This invention relates to new vaccines against microorganisms based on antigenically mimetic peptides. The invention also relates to methods of discovering such mimetic peptides by first screening peptide-display phage libraries with antibodies against the microbial carbohydrates(s) of interest to locate antigenically mimetic peptides. Vaccines against Group B Streptococcus, or *Streptococcus Agalactiae,* are preferably produced using this method.

13 Claims, 3 Drawing Sheets

OTHER PUBLICATIONS

Figure 1A:
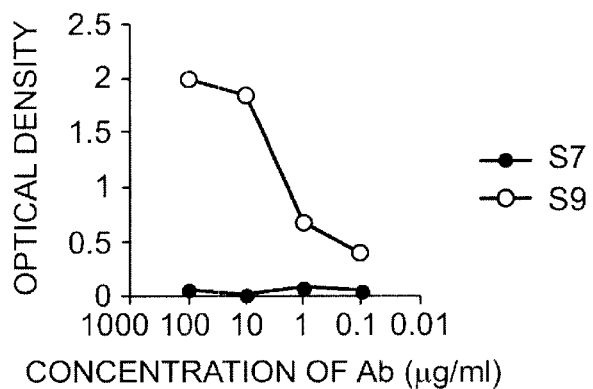

Pincus, S. H., et al., Protective Efficacy of IgM Monoclonal Antibodies in Experimental Group B Streptococcal Infection is a Function of Antibody Avidity, Journal of Immunology, 1988, vol. 140, No. 8, pp. 2779–2785.

Westerink, J., et al., Peptide mimicry of the meningococcal group C capsular polysaccharide, Proc. Natl. Acad. Sci. USA, 1995, vol. 92, No. 9, pp. 4021–4025.

Zou, W., et al., Mimics of the Structural Elements of Type III Group B Streptococcus Capsular Polysaccharide Part III: Two Repeating Units (Octasaccharide) with (S)–1–Carboxyethyl Groups Replacing Sialic Acids, Bioorganic and Medicinal Chemistry Letters, 1997, vol. 7, No. 5, pp. 647–650.

* cited by examiner

SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Mimetic Peptide

<400> SEQUENCE: 1

Phe Asp Thr Gly Ala Phe Asp Pro Asp Trp P ro Ala
 1               5                   10

-continued

```
<210> SEQ ID NO 2
<211> LENGTH: 13
<212> TYPE: PRT
<213> ORGANISM: Artificial Sequence
<220> FEATURE:
<223> OTHER INFORMATION: Description of Artificial  Sequence: Mimetic
      Peptide

<400> SEQUENCE: 2

Phe Asp Thr Gly Ala Phe Asp Pro Asp Trp P ro Ala Cys
  1               5                   10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial  Sequence: Mimetic
      Peptide

<400> SEQUENCE: 3

Trp Glu Asn Trp Met Met Gly Asn Ala
  1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial  Sequence: Mimetic
      Peptide

<400> SEQUENCE: 4

Trp Glu Asn Trp Met Met Gly Asn Ala Cys
  1               5                   10
```

METHOD OF ISOLATING A PEPTIDE WHICH IMMUNOLOGICALLY MIMICS MICROBIAL CARBOHYDRATES INCLUDING GROUP B STREPTOCOCCAL CARBOHYDRATES AND THE USE THEREOF IN A VACCINE

I. STATEMENT OF RELATED APPLICATIONS

This application claims the benefit of U.S. Provisional Application No. 60/070,118, filed Dec. 31, 1997, which is hereby incorporated by reference.

II. FIELD OF THE INVENTION

This invention relates to new vaccines against microorganisms based on antigenically mimetic peptides. The invention also relates to methods of discovering such mimetic peptides by screening peptide-display phage libraries with antibodies against the microbial carbohydrates(s) of interest to locate antigenically mimetic peptides. Vaccines against Group B Streptococcus, or *Streptococcus Agalactiae*, can be produced using this method. Vaccines against other microbial pathogens may also be produced using this method.

III. BACKGROUND OF THE INVENTION

Vaccines protect against disease by harnessing the body's innate ability to protect itself against foreign invading agents. During vaccination, the patient is injected with antigens, or DNA encoding antigens, which generate protective antibodies but which typically cannot cause severe disease themselves. For example, vaccination for bacterial diseases such as typhoid fever consists of injecting a patient with the bacterial agents of these diseases, after they have been disabled in some fashion to prevent them from causing disease. The patient's body recognizes these bacteria nonetheless and generates an antibody response against them.

It is not always possible, however, to stimulate antibody formation merely by injecting the foreign agent which causes the disease. The foreign agent must be immunogenic, that is, it must be able to induce an immune response. Certain agents such as tetanus toxoid are innately immunogenic, and may be administered in vaccines. Other clinically important agents are not immunogenic, however, and must be converted into immunogenic molecules before they can induce an immune response. Successfully accomplishing this conversion for a variety of antigens is a major goal of a great deal of immunologic research.

However, researchers have yet to successfully convert a variety of poorly immunogenic antigens into optimally immunogenic molecules. Of particular importance to the present invention is the failure of immunologic researchers to successfully convert carbohydrates into optimally immunogenic molecules.

Carbohydrates are poorly immunogenic largely because of the way in which they interact with the body's immune system. Carbohydrates frequently function as T-independent antigens, which cannot be properly processed by the antigen presenting cells that begin the typical mammalian immune response. By contrast, T-dependent antigens are initially processed by antigen presenting cells and then rely on T-cells to stimulate B cells to manufacture large quantities of antibodies against the antigen. As a result of these molecular biological differences, T-dependent antigens are immunologically superior to T-independent antigens, including carbohydrates, in three ways:

(1) T-dependent antigens are remembered by the immune system while T-independent antigens are not. Thus, after vaccination, an infection with a T-dependent antigen will be met with an extremely swift and concentrated antibody attack compared to the response to the initial vaccination. Infections with T-independent antigens, by contrast, generally receive the same level of antibody response, even after vaccination;

(2) T-dependent antigens are met with specific antibodies of increasing affinity against them over time, while T-independent antigens are met with antibodies of constant affinity; and (3) T-dependent antigens stimulate a neonatal or immature immune system more effectively than T-independent antigens.

One approach which researchers have taken to enhance the immune response to T-independent antigens is to inject subjects with polysaccharide or oligosaccharide antigens that have been conjugated to a single T-dependent antigen such as tetanus or diphtheria toxoid. (Kasper, D., et al., J. Clin. Invest., Vol. 98, No. 10 2308–2314, 1996) (Schneerson, R. et al., Inf. Immun. 52:519, 1986) (Anderson, P W, et al., J. Immunol. 142:2464, 1989). These conjugate vaccines improve on vaccines based on carbohydrates alone because they "trick" the T-cells into directing the immune response, giving this response something of the character of a T-dependent response, even though it is directed against a T-dependent/T-independent conjugate. However, this "trick" is imperfect—although T-cells do assist, their assistance against conjugates is not as effective as it is against true T-dependent antigens. As a result, generally only low levels of antibody titres are elicited, and only some subjects respond to initial immunizations. Thus, several immunizations are frequently required. This poses a serious obstacle because patients are not always willing, or able, to complete this entire process; this is often true, for example, of patients who live a great distance from medical facilities, as is frequently the case for patients in lesser developed nations. And even when patients do complete the process, there is no guarantee of success—infants less than two months of age may mount little or no antibody response even after repeated immunization. Furthermore, the process itself sometimes takes so long that patients contract the disease in a virulent form before they have been properly vaccinated.

In another attempt to gain the advantages of T-dependent response with T-independent antigens, including carbohydrates, researchers have attempted to discover T-dependent antigens which are structurally related to the T-independent antigen of interest. In theory, these structural mimics might elicit a superior immune response, compared to a vaccine based on either the original T-independent antigen alone or as part of a conjugate. Under this approach, at least, no part of the antigen in the vaccine is incompatible with T-cell assistance.

Yet locating T-dependent antigens which are sufficiently structurally related to T-independent antigens to be true immunological mimics has proven difficult. Researchers have taken three different approaches to this problem, each of which has serious limitations.

First, some researchers have succeeded in designing synthetic peptides which are immunologically mimetic by using computer simulations and protein databases to construct a protein structure which closely resembles the structure of the T-independent antigen of interest, as ascertained through x-ray crystallography. (Westeruik et al., Proc. Nat. Acad. Sci. USA Vol. 92, 4021–4025, 1995). However, this approach is only as good as the researcher's knowledge of the various structures involved, which is frequently far from complete. Furthermore, because even a single amino acid error can have a profound effect on the immunogenicity of the synthetic peptide, as Westernik notes, a very high level of precision is required—higher than may be possible for molecular systems whose structure is not well understood.

Second, some researchers have generated immunologic mimics by isolating anti-idiotypic antibodies which can elicit an immune response to carbohydrate antigens of *S. pneumonia* (McNamara et al., Science 226:1325, 1984), *P. aeruginosa* (Schreiber et al, J. Inf. Dis. 164:507, 1991), *E. coli* (Kacack, M. B. et al., Infec. Immun. 61:2289, 1991) and Group A Streptococci (Manafo, W. J. et al., J. Immunol. 139:2702, 1987). Anti-idiotypic antibodies are known to be structurally similar to the antigens of interest because of their design: they are generated against the idiotypes of antibodies which are known to specifically bind the carbohydrate of interest. As a result, the anti-idiotypic antibody and the carbohydrate bind specifically to the same idiotype structure (an antigenic determining structure in the antigen-binding portion of the carbohydrate binding antibody). Thus, much as two keys which fit the same lock have a high level of structural similarity, anti-idiotypic antibodies are thought to be structurally similar to the antibody-binding structures on carbohydrates. However, the similarity is not complete: these are still antibodies, isolated from the cells of mice, not complete carbohydrate structural mimics. As a result, there has been some concern that, for treatment of humans, human vaccines based on anti-idiotypic antibodies would be undesirable because of serious allergic reactions which could result. (Westernik, M. A. et al., Proc. Nat. Acad. Sci. USA vol. 92, 4021, 1995.) This concern has led at least some researchers to seek alternative means of discovering T-dependent antigens which are structurally similar to T-independent antigens. (Westernik, M. A. et al., Proc. Nat. Acad. Sci. USA vol. 92,4021, 1995).

Finally, some researchers have sought to discover T-dependent antigens which are structurally similar to T-independent antigens by screening libraries of phages, which express hundreds of millions of random peptide sequences, using known carbohydrate-binding antibodies to find particularly promising peptides. (Harris, S. et al., Proc. Natl. Acad. Sci. vol. 94, no. 6 pp. 2454–2459, 1997) (Valuation, P. et al., J. Mol. Biol. 261: 11–22, 1996) (Hoess, R. et al, Gene 128:43, 1993). (See Oldenberg, K. R., Proc. Nat. Acad. Sci. USA 89:5393, 1992 (using lectins to screen such libraries)). The approach outlined in these references is sound only if one accepts that antigenic mimicry (meaning that the peptide mimic binds the same highly specific antibody as the carbohydrate of interest) is reasonably predictive of immunologic mimicry (meaning that the peptide will generate an immune response against the carbohydrate of interest). After all, if antigenic mimics are only rarely immunologic mimics, this procedure leaves one with far more peptide sequence candidates for immunologic testing after the antigenic screening step than can reasonably be tested. Indeed, after several failed attempts at obtaining an immunologic mimic using this approach were conducted, many in the art have in essence concluded that this approach is fundamentally flawed. In particular, at least one researcher has concluded that antigenic mimicry is rarely predictive of true immunologic mimicry, because the mechanism of peptide-antibody binding is different than carbohydrate-antibody binding. (See Harris, S. et al., Proc. Natl. Acad. Sci. Vol. 94 No. 6 pp. 2454–2459, 1997).

Another serious limitation of both this approach and the design-approach of Westernik is that there is no a priori reason to believe that a peptide-based structural mimic necessarily exists for any given carbohydrate. The molecular basis underlying mimicry is unknown, and as such, offers no assurance that all carbohydrates structures have peptide mimics. There is certainly evidence in nature that some carbohydrate structures possess protein mimics. For example, the protein tendamistat is known to bind to the enzyme α-amylase at the same location this enzyme binds carbohydrates. And further research with synthetic peptides has demonstrated a certain level of mimicry in a variety of carbohydrates drawn from a number of species, although the theoretic basis for much of this data has been questioned. (See Harris, S. et al., Proc. Natl. Acad. Sci. vol. 94, no. 6 pp. 2454–2459, 1997). Nevertheless, from these studies, it appears that each new carbohydrate presents a unique challenge to this area of research.

Partly as a result of all of these limitations, there remains a need in the art for vaccines effective against T-independent antigens and a method for developing such vaccines.

This need is particularly acute for vaccines effective against Group B Streptococci (GBS). Efforts at making a vaccine against GBS have focused on using the T-independent polysaccharide of GBS. However, as is frequently the case with T-independent antigens, vaccines containing only GBS polysaccharides have been only marginally effective in inducing antibody. (Baker, C. J. et al., New Eng. J. Med. 319:1180). Conjugate vaccines containing the GBS polysaccharide conjugated to tetanus toxoid, a protein carrier, have been more successful. (Kasper, D. L. et al., J. Clin. Invest. 98:2308). Nevertheless, there is considerable room for improvement in this area of the art.

This unmet need for novel vaccines against Group B Streptococci, or *Streptococcus agalactiae,* is only compounded by the widespread and frequently deadly infections attributed to this bacterial agent. The Center for Disease Control has recently declared prevention of GBS infections a major public health priority. (CDC, Morbidity and Mortality Weekly Report 45 (No. RR-7):1, 1996.) GBS causes invasive infections of newborns, pregnant women, and adults with underlying medical conditions. Although the bacteria are sensitive to antibiotics such as penicillin, case fatality rates are estimated to be 5–20% in newborn children and 15–32% in adults. Infection is most commonly seen as bacteremia, meningitis, and pneumonia. Newborns who survive the disease may suffer permanent neurologic sequelae as a result of meningitis. When mothers lack protective anti-GBS antibodies, their newborn children are at risk of infection. (Baker, C. J. et al, New Eng. J. Med. 294:753, 1976) (Baker, C. J. et al., J. Infect. Dis. 136:598, 1977) (Hemming, V. G. et al., J. Clin. Invest. 58:1379, 1976). The development of maternal vaccines is considered a leading approach to the prevention of GBS disease in newborns. (Mohle-Boetani, J. C. et al., J. Am. Med. Assoc. 270:1442, 1993.) Passive administration of antibody has defined protective epitopes of GBS (Pincus, S. H. et al., J. Immunol. 140:2779, 1988) (Shigeoka, A. O. et al., J. Infect. Dis. 149:363, 1984) (Shigeoka, A. O. et al., Antibiot. Chemother. 35:254, 1985) (Egan, M. L. et al., J. Exp. Med. 158:1006, 1983) (Raff, H. V. et al., J. Exp. Med. 168:905, 1988) (Lancefield, R. C. et al., J. Exp. Med. 142: 165, 1975), responses to which are critical for an effective vaccine.

Thus, there remains in the art a need for improved vaccines against GBS and methods for producing them.

IV. SUMMARY OF THE INVENTION

The present invention addresses this unmet need for novel vaccines by providing a method to isolate a peptide which immunologically mimics GBS. This is the first demonstration that a peptide structural mimic exists for this bacteria.

In addition, this invention meets a more general need in the art because it succeeds in locating mimics where the other two general methods for isolating immunological mimics would fail, or result in suboptimal mimics. First, this invention can succeed in locating an immunologic mimic even when the structure of the carbohydrate antigen is unknown or when an immunologic mimic of that structure cannot be constructed from protein databases and computer simulations, unlike the method of Westernik et al. Second, this invention ultimately results in a vaccine which does not have the same potential for serious allergic reaction possessed by anti-idiotypic antibody based vaccines.

The present invention also offers a validation of the final method to isolating mimetic proteins by contradicting the findings of Harris, et al. Harris concludes that the binding of peptides is by a different mechanism than binding of carbohydrate, and that this is neither antigenic nor immunologic mimicry. (Harris, S. et al., Proc. Natl. Acad. Sci. Vol. 94 No. 6 pp. 2454–2459, 1997.) Harris et al. bases this conclusion on observations made when isolating peptides mimicking group A streptococcal cell-wall polysaccharide. Harris et al. observes that most peptides isolated as potential antigenic mimics were primarily reactive with the antibody used to isolated it, but only weakly reactive with other antibodies against the same cell-wall polysaccharide.

However, the data set forth below contradicts this data, as well as the conclusions drawn from it. In particular, it shows that two out of three IgG monoclonal antibodies to type III GBS also bind to the peptide isolated by the method of the present invention. (FIG. 1b). This data indicates that, while each of the monoclonal antibodies binds to the same polysaccharide structure, some recognize different aspects of that structure. This interpretation was considered by Harris, et al. but discarded in favor of Harris's conclusion that the binding of peptides is by a different mechanism than binding of carbohydrate. (Harris, S. et al., Proc. Natl. Acad. Sci. Vol. 94 No. 6, at 2459, 1997.) Moreover, the data set forth below demonstrates that polyclonal anti-GBS antibodies bind well to the peptide mimetic. Thus the present invention contradicts the Harris findings.

The present invention relates to a method of isolating a peptide which immunologically mimics a portion of Group B streptococci, comprising the steps of:

(1) identifying protective antibodies reactive with said Group B streptococci;

(2) contacting a phage-display library, having phage, with one or more of said protective antibodies identified in step 1;

(3) isolating one or more phage, having a displayed peptide, which bind one or more of the protective antibodies; and (4) selecting, for all said phage isolated in step 3, the peptides or peptide fragments to which the antibodies have bound.

Thus, the invention includes all mimetic peptides and peptide fragments that induce antibodies to GBS. Although any suitable portion of the GBS, such as lipotechoic acid or proteins, may be employed in the invention, in a preferred embodiment, the mimetic peptides induce antibodies against the GBS carbohydrate. In another embodiment, the mimetic peptide induces antibodies to the type III polysaccharide of GBS. In a more preferred embodiment, the invention relates to peptides having the sequence FDTGAFDPDWPA (SEQ ID NO: 1) or FDTGAFDPDWPAC (SEQ ID NO:2) or WENWMMGNA (SEQ ID NO:3) or WENWMMGNAC (SEQ ID NO:4) and fragments and derivatives thereof which exhibit the same or similar ability.

The present invention also relates to a vaccine consisting of these peptides and/or peptide fragments and/or derivatives together with a pharmaceutically acceptable carrier.

In yet another embodiment, the peptides and/or peptide fragments and/or derivatives of the invention may be conjugated to a carrier. In a further embodiment, multiple copies of the peptide are used. In another embodiment, a fusion protein containing the peptide is employed. In yet another embodiment, the vaccine uses DNA encoding for the peptide, the conjugate, or the fusion protein.

The present invention also relates method of treating a patient, comprising administering to the patient an immunostimulatory amount of the vaccine of the invention.

V. BRIEF DESCRIPTION OF THE DRAWINGS

Figure 1B:
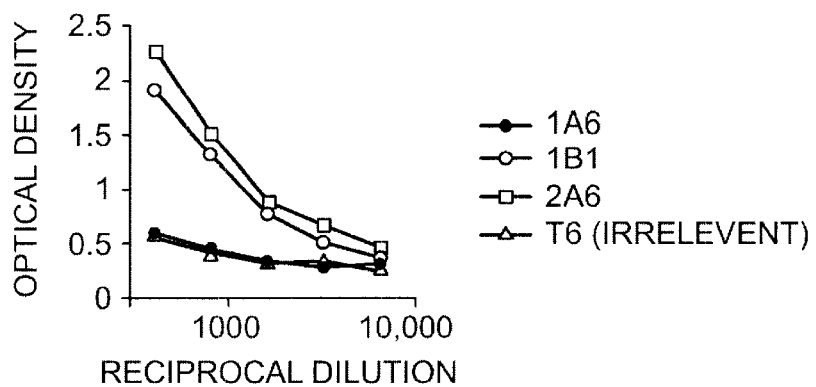
Figure 1C:
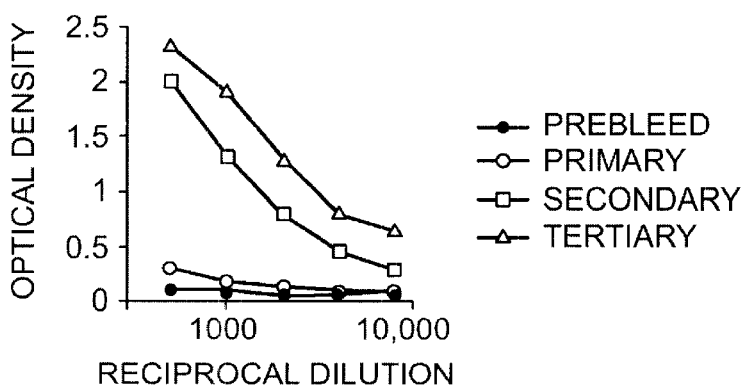

FIG. 1 Binding of antibodies to synthetic peptide FDTGAFDPDWPAC (SEQ ID NO:2).

Microtiter wells were coated with peptide at 10 $\mu$g/ml and then blocked with 1% BSA. Test antibodies were added to the wells, incubated and washed. Antibody binding was detected with alkaline phosphatase conjugated anti-Ig and then substrate. The values are $A_{405}$, mean of duplicate or triplicate samples. The binding of monoclonal antibodies S7 and S9 is shown in panel A. Panel B shows the binding of three IgG anti-GBS type III and one irrelevant monoclonal antibodies, and panel C shows the serum from mice infected with $10^8$ live GBS type III (primary, secondary, and tertiary refer to the number of times the mice were infected). The binding of all antibodies to BSA was<0.1.

FIG. 2 Competitive inhibition assays. Panel A shows inhibition of S9 binding to GBS by peptide. Antibodies S7 or S9 were diluted to the concentrations shown and mixed with the indicated concentration of peptide FDTGAFDPDWPAC (SEQ ID NO:2). Following a one hour incubation, the peptide and antibody were transferred to GBS-coated microtiter wells, and incubated overnight. The plates were washed and antibody binding was detected with alkaline phosphatase-conjugated anti-mouse IgM and substrate. The values are $A_{405}$, mean of duplicate samples. Panel B shows the inhibition of anti-GBS antiserum (secondary bleed from panel 1 C) binding to FDTGAFDPDWPAC (SEQ ID NO:2). The indicated dilutions of serum were mixed with intact GBS or purified type III capsular polysaccharide (III-CPS) and plated into peptide-coated wells. The plates were washed and antibody binding was detected with alkaline phosphatase anti-mouse Ig and substrate. The values are the mean and SEM of triplicate samples (if no error bars are seen, the SEM is too small to be drawn).

Figure 3:
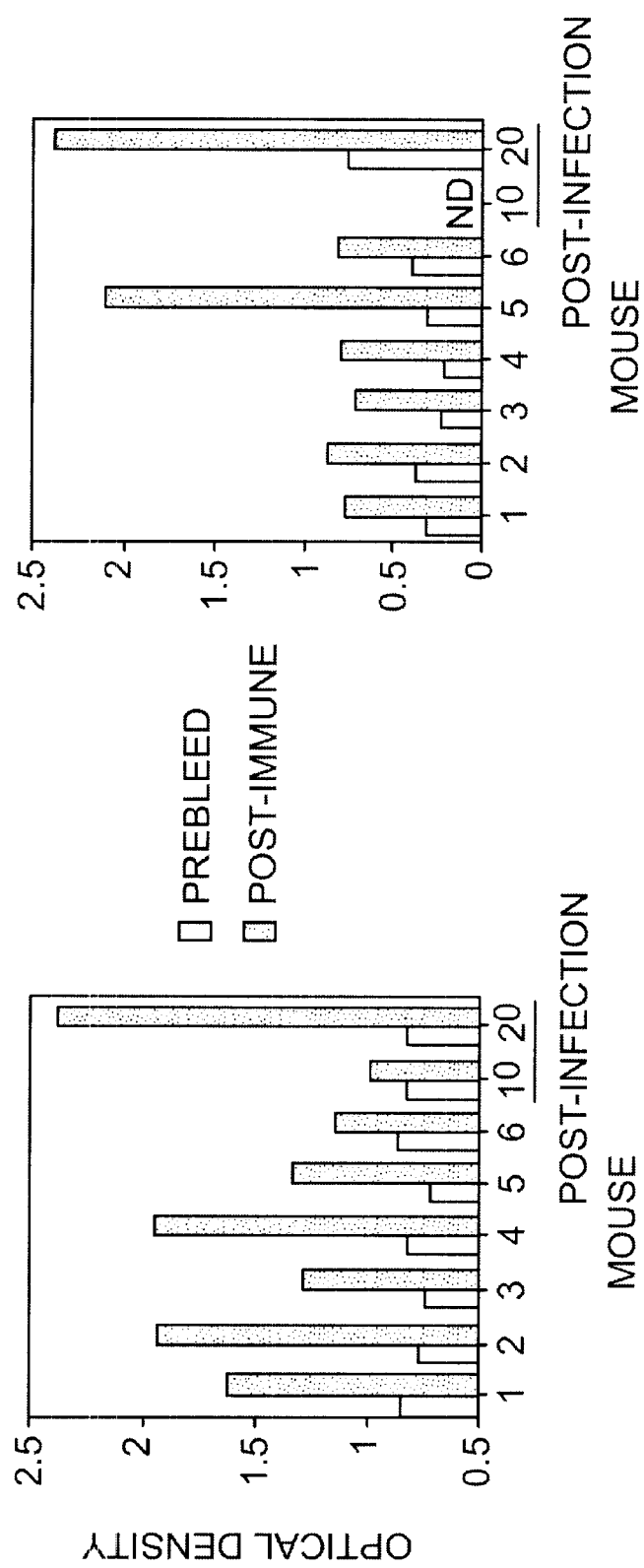

FIG. 3 Immunization of mice with peptide-carrier conjugates results in the production of GBS antibodies. Mice were immunized with peptide FDTGAFDPDWPAC (SEQ ID NO:2) conjugated to OVA (mouse 1 and 2), KLH (mouse 3 and 4), or BSA (mouse 5 and 6), or with live GBS, once (1°) or twice (2°). Both prebleed and post-immune sera were diluted 1:1000 and tested for binding to type III GBS (left panel) or to type III capsular polysaccharide (right panel).

VI. DETAILED DESCRIPTION OF THE INVENTION

In developing the invention, the inventor used monoclonal antibody S9, a protective IgM monoclonal antibody against the type III capsular polysaccharide (III-CPS) of Group B Streptococci (GBS) was used (Christensen, R. D.

et al., Pediatr. Res. 17:795, 1983) (Pincus, S. H. et al, J. Immunol. 140:2779, 1988) (Shigeoka, A. O. et al, J. Infect. Dis. 149:363, 1984) to select epitope analogues from a peptide-display phage library. The library consisted of millions of phage expressing different fusion proteins from their surface. Depending upon desorption conditions, two populations of phage were identified with displayed sequences of WENWMMGNA (SEQ ID NO:3) and FDTGAFDPDWPA. (SEQ ID NO:1) (Example 1) Both sequences have aromatic, acidic, and hydrophobic residues. The presence of aromatic residues is characteristically seen in peptides mimicking carbohydrates. (See Westernik, M. A. et al, Proc. Natl. Acad. Sci. USA 92:4021 at 4025, 1995.) The presence of acidic residues probably reflects the sialic acid in the carbohydrate epitope. However the molecular basis underlying the antigenic mimicry of the carbohydrate structure by the peptides is not known and this description is not intended to limit the invention.

As the study progressed, ELISA results demonstrated that phage with these two displayed sequences bound to S9 and no other antibodies. (Example 2.) Phage blocked the binding of S9 to type III GBS, but did not block the binding of another anti-GBS monoclonal antibody. (Example 3.) Phage displaying the FDTGAFDPDWPA (SEQ ID NO:1) sequence showed greater inhibition. (Example 3.) Antibody S9 and other monoclonal and polyclonal anti-GBS type III antisera bound the synthetic peptide FDTGAFDPDWPAC (SEQ ID NO:2). (Example 3.) The binding of S9 to GBS was inhibited by the free peptide with an $IC_{50}$ of 30 $\mu$g/ml. (Example 3.) The binding of polyclonal anti-GBS antibodies to peptide could be blocked by intact GBS, as well as by purified capsular polysaccharide. (Example 4.) The peptide was conjugated to three different carriers and used to immunize mice. (Example 5.) All mice produced a significant antibody response to GBS and to the purified capsular polysaccharide following a single immunization. (Example 5.) These data demonstrate that a peptide mimetic of the GBS capsular polysaccharide is both antigenic and immunogenic. Such peptides will provide more efficacious vaccine preparations against important carbohydrate epitopes.

Thus, the present invention relates to a method of isolating a peptide which immunologically mimics a portion of Group B streptococci, comprising the steps of:

(1) identifying protective antibodies reactive with said Group B streptococci;

(2) contacting a phage-display library, having phage, with one or more of said protective antibodies identified in step 1;

(3) isolating one or more phage, having a displayed peptide, which bind one or more of the protective antibodies; and (4) selecting, for all said phage isolated in step 3, the peptides or peptide fragments to which the antibodies have bound.

A peptide which "immunologically mimics" GBS is a substance that elicits an antibody response against the GBS. The peptide is preferably greater than five amino acids, although peptides of any length are within the scope of the invention.

The protective antibodies within the invention are antibodies shown to protect against GBS infection or to ameliorate the effects of a GBS infection. Any bactericidal assay that is known in the art may be used to identify the protective antibodies of the invention, although the assay set forth in U.S. Pat. No. 5,971,511, is preferred. In addition, protective antibodies can be identified by use of the lethal challenge assay in which laboratory animals, generally mice, are injected with a lethal amount of the bacteria being tested. Antibodies are then administered and mouse survival is determined. Those antibodies that are able to protect against death are considered to be protective.

"Contacting", as used herein, refers to incubation for a sufficient period of time to permit antibody/antigen binding to occur, as can be easily measured by methods routine in the art.

"Phage display library", as used herein, refers to a multiplicity of phage which express random amino acid sequences of between 7 and 15 amino acids at a location which may be bound by an antibody.

Particularly preferred in the practice of this invention is a phage display library produced by the method of Burritt et al. (Burritt, J. B. et al., Analyt. Biochem. 338:1). Phage has the usual meaning it is given by one of ordinary skill in the art. (See, for example, Maniatis, et al., Molecular cloning: a laboratory manual. Cold Spring Harbor (1982))

The phrase "antibodies specific for GBS" refers to monoclonal or polyclonal antibodies which bind the substance GBS with an affinity greater than the average unselective affinity which these antibodies show for substances structurally unrelated to GBS. Although antibodies of all isotypes, i.e., IgG, IgA, IgM, IgD, and IgE, may be used, in one embodiment, IgM antibodies are preferred.

A particularly preferred antibody in the practice of this invention is monoclonal antibody S9, a protective monoclonal antibody of the IgM isotype against the type III capsular polysaccharide of group B Streptococci.

As noted above, any portion of the Group B streptococci, such as lipotechoic acid or proteins, may be used but the preferred portion is the carbohydrate. A preferred carbohydrate is the capsular polysaccharide, and a particularly preferred capsular polysaccharide is the Type III capsular polysaccharide (associated with Type III Group B Streptococcus), although Type I and Type II are within the scope of the invention.

The phrase "isolating one or more phage . . . which bind one or more of the antibodies" means physically removing from the phage display library phage that bind the antibody with greater affinity than that between the antibody and a structurally unrelated antigen.

Although any technique for isolation may be used in the practice of the invention, a preferred method is affinity purification, which is well known in the art. A particularly preferred means of isolating phage from the phage display library is to first preabsorb the library repeatedly with cyanogen bromide activated sepharose 4B beads coated with antibodies specific for an antigen structurally unrelated to Group B Streptococcus capsular polysaccharide, most preferably S10 antibody. Following repeated preabsorption, the library is incubated overnight with cyanogen bromide activated sepharose 4B beads coated with one or more antibodies specific for Group B Streptococcus. Following this incubation, these same beads are washed extensively, and then eluted into two separate pools, the first pool being formed by elution with 0.1M glycine pH 2.2, with the second being formed by elution with 0.5M $NH_4OH$ pH 7. Next, the eluated pools are amplified, most preferably in *E. coli* strain K91. Following elution, each pool is reapplied to the column, and the same incubation and washing procedure employed, eluting (in the end) with the same substance used to generate the original pool. This process is repeated for each pool, most preferably three times. Finally, phage are tested for binding to the selecting antibody using immunoblots of plaques. Phage which pass this final round are cloned, amplified to high titer, and purified by precipitation, most preferably with 2.5% polyethylene glycol.

"Displayed peptide" refers to peptides having an amino-acid sequence of between 7 and 15 amino acids which varies randomly between each of the individual phage which make up the phage display library.

As noted above, the mimetic peptides obtained by this method may induce antibodies to any portion of the GBS, but preferably to a carbohydrate portion. Even more preferable are peptides that induce antibodies to capsular polysaccharides of GBS, including Type III. Specific peptides within the invention are FDTGAFDPDWPA (SEQ ID NO:1) or FDTGAFDPDWPAC (SEQ ID NO:2) or WENWMMGNA (SEQ ID NO:3) or WENWMMGNAC (SEQ ID NO:4), but the invention also includes fragments and derivatives thereof that exhibit the same or similar activity.

Once the peptides are isolated by this process, they may be used in a vaccine. The vaccine may include the peptide itself or the peptide may be conjugated to a carrier or otherwise compounded. Carrier preferably refers to a T-dependent antigen which can activate and recruit T-cells and thereby augment T-cell dependent antibody production. However, the carrier need not be strongly immunogenic by itself, although strongly immunogenic carriers are within the scope of this invention. Multiple copies of the carrier are also within the scope of this invention. Multiple copies of the peptide are also within the scope of the invention, either unconjugated or conjugated to one or more copies of the carrier. Fragments and derivatives of the peptide are also within the scope of the invention, either alone or in combination with each other, not necessarily identically reproduced, and either unconjugated or conjugated to one or more copies of the carrier. Fusion proteins containing single or multiple copies of the peptide or parts thereof are also within the scope of the invention. In a further embodiment, microbes that express the DNA of the fusion protein are within the invention. In yet another embodiment, DNA encoding any and all of these substances is within the scope of the invention.

In a preferred embodiment, the carrier is a protein, a peptide, a T cell adjuvant or any other compound capable of enhancing the immune response. The protein may be selected from a group consisting of but not limited to viral, bacterial, parasitic, animal and fungal proteins. In a more preferred embodiment, the carrier is albumin (such as bovine serum albumin (BSA)), keyhole limpet hemocyanin (KLH), ovalbumin (OVA), tetanus toxoid, diphtheria toxoid, or bacterial outer membrane protein, all of which may be obtained from biochemical or pharmaceutical supply companies or prepared by standard methodology (Cruse, J M (ed.) Conjugate Vaccines in Contributions to Microbiology and Immunology vol. 10 (1989)). Other proteins that could function as carriers would be known to those of ordinary skill in the art of immunology.

The isolated peptides, with or without further compounding, may be immunogenic or, alternatively, the immunogenicity may arise from the compounding. Methods of measuring immunogenicity are well known to those in the art and primarily include measurement of serum antibody including measurement of amount, avidity, and isotype distribution at various times after injection of the construct. Greater immunogenicity may be reflected by a higher titer and/or increased life span of the antibodies. Immunogenicity may also be measured by the ability to induce protection to challenge with noxious substance or organisms. Immunogenicity may also be measured using in vitro bactericidal assays as well as by the ability to immunize neonatal and/or immune defective mice. Immunogenicity may be measured in the patient population to be treated or in a population that mimics the immune response of the patient population.

A particularly preferred means of determining the immunogenicity of a given substance is to first obtain sera of mice both before and after immunization with the substance. Following this, the strength of the post-immunization sera binding to GBS and capsular polysaccharide is ascertained using an ELISA, and compared against the ELISA results obtained for the pre-immunization sera.

The peptides of the invention as well as the vaccines of the invention may exhibit enhanced immunogenicity. Enhanced immunogenicity refers to immunogenicity greater than that obtained by the Group B Streptococcal carbohydrate of interest alone, and preferably that sufficient to effect a statistically measurable immunoprotective effect. As a point of reference, a peptide would certainly have enhanced immunogenicity if it provoked a level of immunogenic response equal to or greater than that obtained by administration of purified carbohydrate. In a preferred embodiment, the enhanced immunogenicity, as measured by an ELISA, is greater than that provoked by $10^8$ GBS, and comparable to that seen after two injections with live GBS.

Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in Martin, E. W., Remington's Pharmaceutical Sciences, specifically incorporated herein by reference. These carriers can also contain immunoadjuvants, including but not limited to alum, aluminum compounds (phosphate and hydroxide), and muramyl dipeptide derivatives.

The invention also relates to the treatment of a patient by administration of an immunostimulatory amount of the vaccine. Patient refers to any subject for whom the treatment may be beneficial and includes mammals, especially humans, horses, cows, dogs, and cats as well as other animals, such as chicks. An immunostimulatory amount refers to that amount of vaccine that is able to stimulate the immune response of the patient for the prevention, amelioration, or treatment of diseases. Of course, as noted above, the immunostimulation may result from the form of the antibody or the adjuvant with which it is compounded.

The vaccine of the invention may be administered by any route, but is preferably administered topically, mucosally or orally. Other methods of administration will be familiar to those of ordinary skill in the art, including intravenous, intramuscular, intraperitoneal, intracoporeal, intrarticular, intrathecal, intravaginal, intranasal, oral and subcutaneous injections.

All references cited in the specification are hereby explicitly incorporated by reference, even if no language in the citation itself so indicates.

Methods

I. Antibodies, Bacteria, Phage Library and Peptide.

The murine monoclonal antibodies used in this study are listed in Table I, below. Antibodies S7, S9, and S10 are IgM antibodies against GBS (Pincus, S. H. et al., J. Immunol. 140:2779), B6.1 is a protective IgM antibody directed against a β-1,2-linked trimannose epitope of *Candida albicans,* (Han, Y. et al., Infect. Immun. 63:2714), and 924 is an irrelevant IgGI anti-HIV gp120 (Pincus, S. H. et al., J.

Immunol. 146:4315). Antibodies 1A6, 1B1, and 2A6 were produced by immunization with tetanus toxoid-type III capsular polysaccharide conjugate. (Jennings, H. J., manuscript in preparation). Polyclonal anti-type III GBS antiserum was obtained by repeated infection of BALB/c mice with $10^8$ live GBS strain 1.2 as described elsewhere (Pincus, S. H. et al. Infect. Immun.. 61:3761). Mice were bled 18 days following the first infection (primary bleed) and one week following the second and third infections. Rabbit antiserum against M13 bacteriophage was made in our laboratories. Alkaline phosphatase-conjugated anti-mouse IgG and anti-rabbit IgG were from Zymed Laboratories (South San Francisco, Calif.). GBS type III, strain 1.2, are described elsewhere. (Pincus, S. H. et al., J. Bacteriol. 174:3739). Capsularpolysaccharide was extracted from GBS strain 1.2 using a modification of the protocol of Lancefield (Lancefield, R. C. J. Hyg. (Lond.) 64:191). GBS were washed twice in water, boiled in HCl pH 2.0 for 10 minutes, and the GBS pelleted out. The HCl extract was neutralized with tris base, chilled and precipitated with 80% ethanol. The ethanol extract was then treated with DNAase (5 $\mu$g/ml), RNAase (1 $\mu$g/ml), and then proteinase k (200 $\mu$g/ml). The extract was bound by antibody S9, but not by S7 indicating the presence of type III capsular antigen, but not group B carbohydrate. The phage display library utilized in these studies was produced by Dr. J. Burritt in the filamentous phage M13KBst and express a random 9AA peptide sequence as an amino-terminal fusion with the minor coat protein pIII. (Burritt, J. B. et al., Analyt. Biochem 338:1) (Deleo, F. R. et al., Proc. Nat. Acad. Sci. USA. 92:7110) (Smith, G. P. et al, Methods in Enzymology 217:228). The library has a complexity of $5\times10^8$ unique phage. The amino acid sequence of the displayed peptide was derived by sequencing the chimeric pIII-peptide gene utilizing automated sequencing methodology (University of Montana Molecular Biology Center, Missoula, Mont.). A synthetic peptide of sequence FDTGAFDPDWPAC (SEQ ID NO:2) was made by the company Bio-Synthesis (Lewisville, Tex.) using standard F-moc solid phase synthesis protocols and was>70% pure by HPLC and mass spectrometer analysis.

TABLE I

Antibodies

| Name | Class | Specificity | Reference |
|------|-------|-------------|-----------|
| S7 | IgM | group B carbohydrate, all GBS | (Pincus, S. H. et al., J. Immunol. 140:2779, 1988) |
| S9 | IgM | type III capsular polysaccharide | (Pincus, S. H., et al., J. Immunol. 140:2779, 1988) |
| S10 | IgM | Beta-C protein of type I and II GBS | (Pincus, S. H., et al., J. Immunol. 140:2779, 1988) |
| 1A6 | IgG1 | type III capsular polysaccharide | (Jennings, H. J., manuscript) |
| 1B1 | IgG2a | type III capsular | (Jennings, H. J., manuscript) |
| 2A6 | IgG1 | type III capsular polysaccharide | (Jennings, H. J., manuscript) |
| 924 | IgG1 | HIV gp120 | (Pincus, S. H., et al., J. Immunol. 146.4315, 1991) |
| B6.1 | IgM | *Candida albicans* | (Han, Y., et al., Infect. Immun. 63:2714, 1995) |
| T6 | IgG1 | Synthetic polypeptide (Y,E)-A–K | (Pincus, S. H., et al., Mol. Immunol. 19:1551, 1982) |

II. Selection of Phage

Monoclonal antibodies S7, S9, and S10 were separately immobilized on cyanogen bromide activated SEPHAROSE™ 4B beads (Sigma Chemical, St. Louis, Mo.) at 3 mg of antibody per ml of beads. Phage ($4\times10^{12}$ plaque forming units, pfu) were preadsorbed five times on beads containing immobilized antibody S10 to remove any phage that would bind to all IgM antibodies. The preadsorbed library was divided into two aliquots, for affinity selection with either antibody S7 or S9. The phage, diluted in tris buffered saline (TBS), 1% bovine serum albumin (BSA), and 1% Tween-20, were incubated overnight with 2.5 ml of immobilized antibody. The beads were washed extensively with TBS/Tween (15 batchwise elutions of 15 ml each and on a column with 75 ml) and eluted with 0.1 M glycine pH 2.2. Following an additional wash, the beads were further eluted with 0.5 M $NH_4OH$ pH 11. The eluted phage were neutralized to pH 7 immediately, and those phage eluted with high or low pH were maintained as distinct pools. The titer of phage in the last wash and each eluate was determined. The eluted phage were then amplified in *E. coli* strain K91 to a titer of $10^{12}$ pfu and reapplied to the column. The same incubation and washing procedures were used, and bound phage eluted with either glycine or $NH_4OH$, depending upon which pool of phage was used. Each aliquot of phage was subjected to three such rounds of selection. The third round eluate had>$10^8$ pfu. Phage were tested for binding to the selecting antibody, but not to irrelevant IgMs using immunoblots of plaques. Phage with the desired reactivity were cloned, amplified to high titer, and purified by precipitation with 2.5% polyethylene glycol (8000 MW), 0.5M NaCl.

III. ELISA

ELISA was used to measure the binding of phage to antibody, antibody to peptide, and antibody to GBS or capsular polysaccharide. Protein or peptide antigens were coated onto microtiter wells (Immulon 2, Dynatech, McLean, Va.) at 5–10 $\mu$g/ml. GBS were coated onto microtiter wells using poly-l-lysine and glutaraldehyde as described elsewhere. (Pincus, S. H. et al., J. Immunol. 140:2779) (Pincus, S. H. et al., Infect. Immun. 61:3761). Capsular polysaccharide was coated directly onto microtiter wells. Plates were blocked with 1% BSA or 1% ovalbumin (OVA) and used within one week. Primary antibodies were incubated in microtiter wells at 40 for 18 hours. The plates were washed and incubated with alkaline phosphatase-conjugated anti-Ig for 6 hours, followed by washing and addition of colorimetric substrate p-nitrophenyl phosphate (Sigma Chemical). $A_{405}$ was determined using a microplate reader (EL-320, Bio-Tek Instruments, Winooski, Vt.). Binding of phage was measured by incubating phage in coated microtiter wells, washing, addition of rabbit anti-phage antiserum, and detection of rabbit Ig with alkaline phosphatase-conjugated anti-rabbit Ig.

IV. Immunization of Mice

Peptide was conjugated to maleimide-derivitized BSA, OVA, and keyhole limpet hemocyanin (KLH, Pierce Chemical, Rockford, Ill.). Efficacy of conjugation was demonstrated by reactivity of the conjugate, but not the unconjugated maleimide derivative, with antibody S9. Three groups of two mice were immunized subcutaneously with a single 50 $\mu$g dose of each conjugate in complete Freund's adjuvant (DIFCO, Detroit Mich.). Mice were bled on the day of immunization and day 35.

EXAMPLE 1

Selection of Phage

A phage-display library expressing a random nine AA sequence was selected for binding to one of two different anti-GBS monoclonal antibodies: S9, a protective monoclonal antibody that binds to the type III capsular polysaccharide, and S7, specific for the group B carbohydrate. (Pincus, S. H. et al., J. Immunol. 140:2779). The latter was used primarily as a specificity control. Within each selection, two separate desorption protocols were used to identify two populations of phage: 0.1 M glycine pH 2.2 or 0.5M NH$_4$OH pH 11. Phage with binding specificity for the selecting antibody were identified by immunoblots of plaques. Forty clones were selected, ten from each elution condition and selecting antibody, and amplified to a titer of $10^{13}$–$10^{14}$ pfu/ml.

The DNA encoding the displayed peptide from the two different pools of S9-selected phage was sequenced. Within each pool, the sequence of each clone was identical, but two very different sequences were seen depending upon the eluting pH. The 9AA displayed sequence for the glycine pH 2.2 eluted phage was WENWMMGNA (SEQ ID NO:3). The sequence displayed by the NH$_4$OH-eluted phage was 12 AA long because there was a single base deletion following the sequence encoding the displayed peptide followed 8 bases later by a compensatory single base addition. The 12 AA sequence displayed by the NH$_4$OH-eluted phage was FDT-GAFDPDWPA (SEQ ID NO: 1). Although these two sequences are considerably different, there are similarities in motif, in each case there are aromatic, acidic and hydrophobic residues.

EXAMPLE 2

Specificity of Antibody Binding to Displayed Peptides

To show the specificity of phage binding, ELISA plates were coated with antibodies. The immobilized antibodies were incubated with representative phage clones from each selection ($10^{10}$ pfu per well) and binding measured. The results are shown in Table II, below. The parental phage (M13KBst) bound to no antibody. Phage selected with antibody S7 or S9 bound only to the selecting antibody. Phage that were first absorbed on antibody S10, prior to the selection on S7 or S9, bound to all IgM antibodies, indicating that within the library there is a population of phage that bind to all IgMs.

TABLE II

Binding of Phage to Immobilized Antibodies.

| | | ANTIBODY | | | | |
|---|---|---|---|---|---|---|
| Phage | Selection | None | 924 | S7 | S9 | B6.1 |
| M13KBst | none | 0.05 | 0.12 | 0.12 | 0.08 | 0.16 |
| S10-4 | S10 | 0.08 | 0.13 | 1.62 | 1.54 | 2.41 |
| S10-8 | S10 | 0.09 | 0.22 | 1.84 | 1.88 | 2.42 |
| S9-11 | S9-pH 2.2 | 0.05 | 0.16 | 0.10 | 1.22 | 0.17 |
| S9-16 | S9-pH 2.2 | 0.19 | ND | 0.18 | 1.15 | 0.10 |
| S9-26 | S9-pH 11 | 0.06 | ND | 0.15 | 1.80 | 0.07 |
| S9-24 | S9-pH 11 | 0.03 | 0.07 | 0.07 | 1.76 | 0.15 |
| S7-A | S7-pH 11 | 0.05 | 0.10 | 1.74 | 0.16 | 0.20 |
| S7-B | S7-pH 2.2 | 0.08 | ND | 1.91 | 0.28 | 0.49 |

The indicated antibodies were coated onto wells of microtiter plates at 5 μg/ml. Phage ($10^{10}$ pfil) were incubated with the antibody for 18 hours at 4 °. The selection used to isolate each pool of phage is identified by the selecting antibody and the desorption condition. Phage binding to antibody were detected with rabbit anti-M13 antiserum, then alkaline phosphatase-conjugated anti-rabbit Ig, and p-nitrophenyl phosphate substrate. The values are A$_{405}$, mean of duplicate samples.

Binding of antibodies to the synthetic peptide FDT-GAFDPDWPAC (SEQ ID NO:2) was also demonstrated by ELISA. FIG. 1 shows the binding of the antibodies to peptide. Panel A shows binding of the monoclonal antibodies S7 and S9. Binding to the peptide was seen only with antibody S9. Panel B shows that two of three other IgG anti-GBS type III monoclonal antibodies bind to the peptide. Panel C shows that the sera of mice infected with type III GBS bind to the peptide; binding to the peptide parallels the total antibody response to type III GBS (Pincus, S. H. et al., Infect. Immun. 61:3761). These data demonstrate that anti-GBS antibodies other than the selecting antibody also recognize the peptide sequence.

EXAMPLE 3

Phage and Peptides Block the Binding of Antibody to GBS

The demonstration of specific recognition of the peptide sequence by the selecting antibody is a good indication that the phage bind to the variable regions. However to demonstrate that the displayed sequence actually resembles the carbohydrate epitope of GBS, blocking of antibody binding to GBS antigens must be shown. To perform these experiments, ELISA was used where antibody and inhibitor (phage or peptide) were premixed, incubated for one hour, and then plated onto the microtiter plates with GBS. Inhibition of the antibody's binding to GBS indicated that the phage or peptide was successfully competing with the GBS for antibody binding.

In Table III, below, intact phage were used to inhibit the binding of antibodies S7 and S9 to GBS. The concentrations of S7 used were slightly higher than those of S9 because there are fewer antigenic determinants recognized by S7 on the surface of GBS. (Pincus, S. H. et al., J. Immunol. 140:2779). The concentrations of antibody used for inhibition are in middle third of the linear portion of the binding curve. Antibody B6.1 was used to indicate the level of background binding of IgM to GBS. The S9-selected phage inhibited the binding of S9 but not S7 to GBS, while the S7-selected phage inhibited the binding of only S7. The parental phage did not produce significant inhibition of either S7 or S9. In some cases, the inhibition of antibody binding was virtually complete. The inhibition of S9 induced by the phage eluted at high pH (S9-24 and S9-26) was considerably greater than that seen with the phage eluted at low pH. To confirm that the phage eluted at high pH were better inhibitors, a titration of phage was performed. (Table IV). The data indicate that the phage eluted at high pH were approximately five times more efficient at inhibiting antibody S9 as the low pH phage; equivalent inhibition was seen with 2×$10^{10}$ pfu S9-24 or S9-26 as with $10^{11}$ pfu S9-11 or S9-16. The greater inhibition maybe a reflection of the AA sequence of the displayed peptide or of its greater length. The increased inhibition is an indication that the peptide displayed by phage clones S9-24 and S9-26 binds to antibody S9 with a higher avidity than the other displayed peptides.

TABLE III

Inhibition by phage of antibody binding to GBS

| | S9 (μg/ml) | | S7 (μg/ml) | |
|---|---|---|---|---|
| Inhibitor | 0.1 | 0.03 | 0.3 | 0.1 |
| no phage | 2.03 | 0.63 | 2.25 | 0.93 |
| M13KBst | 1.97 | 0.51 | 2.04 | 0.97 |

TABLE III-continued

Inhibition by phage of antibody binding to GBS

| | S9 (µg/ml) | | S7 (µg/ml) | |
|---|---|---|---|---|
| Inhibitor | 0.1 | 0.03 | 0.3 | 0.1 |
| S9-11 | 1.47 | 0.16 | 2.41 | 1.07 |
| S9-16 | 0.89 | 0.14 | 1.94 | 1.10 |
| S9-24 | 0.15 | 0.13 | 2.23 | 1.17 |
| S9-26 | 0.21 | 0.14 | 2.47 | 1.02 |
| S7-A | 1.96 | 0.55 | 0.48 | 0.30 |

Antibodies S7 or S9 were diluted to the concentrations shown and mixed with $10^{11}$ pfu of the indicated phage. Following a one hour incubation, the phage and antibody were transferred to GBS-coated microtiter wells, where they were incubated overnight. The plates were washed and antibody binding was detected with alkaline phosphatase-conjugated anti-mouse IgM and substrate. The values are $A_{405}$, mean of duplicate samples. Background binding of irrelevant IgM antibody B6.1 is 0.14.

TABLE IV

Titration of phage-mediated inhibition of antibody binding to GBS

| Phage | Number | Ab Binding |
|---|---|---|
| None | 0 | 2.03 |
| M13KBst | $10^{11}$ | 1.97 |
| S9-11 | $10^{11}$ | 1.47 |
| | $2 \times 10^{10}$ | 1.66 |
| S9-16 | $10^{11}$ | 0.89 |
| | $2 \times 10^{10}$ | 1.54 |
| S9-24 | $10^{11}$ | 0.15 |
| | $2 \times 10^{10}$ | 1.03 |
| S9-26 | $10^{11}$ | 0.21 |
| | $2 \times 10^{10}$ | 1.34 |

Antibody S9 (0.1 µg/ml) was mixed with the indicated number (pfu) of phage, incubated for one hour, transferred to GBS coated microtiter wells, and incubated overnight. The plates were washed and antibody binding was detected with alkaline phosphatase-conjugated anti-mouse IgM and substrate. The values are $A_{405}$, mean of duplicate samples.

Because inhibition of antibody binding seen with intact phage may have resulted from steric inhibition due to the large size of a filamentous phage, the inhibition experiments were repeated with the synthetic peptide FDTGAFDPDWPAC (SEQ ID NO:2). Those results are shown in FIG. 2, panel A. The binding of S9 to GBS was inhibited by free peptide with an $IC_{50}$ of approximately 30 µg/ml. There was no inhibition of the binding of antibody S7.

EXAMPLE 4

Binding of Anti-GBS Antibody to Peptide is Inhibited by Capsular Polysaccharide

Figures 2A, 2B:
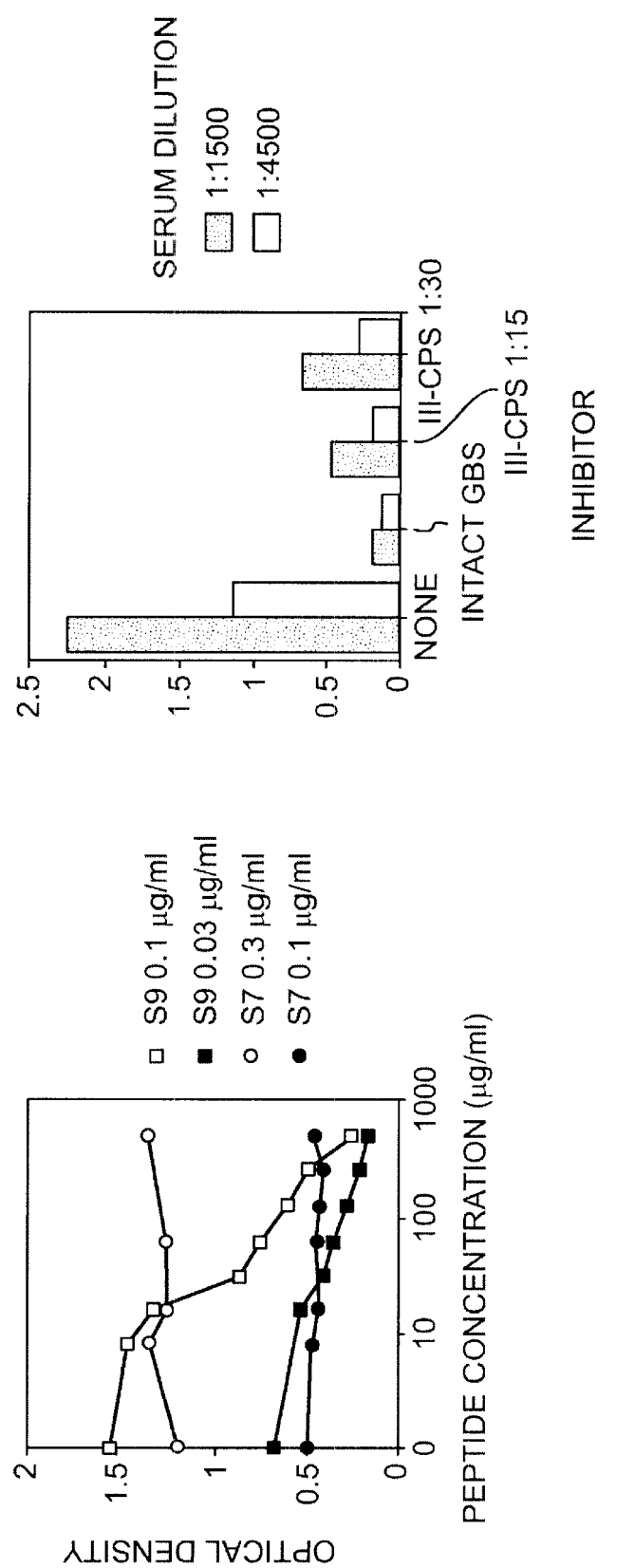

To demonstrate that anti-GBS polyclonal antibodies which bind to the peptide are specific for the type III capsular polysaccharide, both intact GBS and extracted capsular polysaccharide were used to inhibit binding to peptide (FIG. 2B). Two different dilutions of sera from mice infected with GBS were premixed with either an equal volume of GBS (OD 0.9) or dilutions of the capsular polysaccharide. The GBS gave complete inhibition of binding to peptide. Although the inhibition by the capsular polysaccharide was not quite complete, the increasing inhibition with greater concentrations of polysaccharide or lesser amounts of serum suggest that the maximal inhibition had not been obtained.

EXAMPLE 5

Mice Immunized with Peptide Make Anti-GBS Antibody

Mice were immunized with peptide FDTGAFDPDWPAC (SEQ ID NO:2) conjugated to OVA (mouse 1 and 2), KLH (mouse 3 and 4), or BSA (mouse 5 and 6), or with live GBS, once (1°) or twice (2°). Conjugation can be accomplished using standard methodology. (See Cruse, J M (ed.) Conjugate Vaccines in Contributions to Microbiology and Immunology vol. 10 (1989)). Both prebleed and post-immune sera were diluted 1:1000 and tested for binding to type III GBS or to type III capsular polysaccharide. All mice made peptide-specific antibody as well as antibody to GBS and to purified capsular polysaccharide as shown in FIG. 3. The left panel shows binding to type III GBS and the right panel shows binding to type III capsular polysaccharide. The results demonstrate a high background of binding to GBS in the prebleed sera, perhaps as a result of binding to bacterial Fc receptors. As a comparison, the anti-GBS antibody response of mice that were infected with live GBS was also measured. A single immunization with peptide-protein conjugate induced a greater anti-GBS antibody response than seen following infection with $10^8$ GBS and a response comparable to that seen following a second infection.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A peptide that induces an immunoprotective response against Group B Streptococci Type III, wherein said peptide specifically binds to an antibody that specifically binds to Group B Streptococci Type III capsular polysaccharide.

2. The peptide of claim 1, having a sequence selected from the group consisting of FDTGAFDPDWPA (SEQ ID NO: 1), FDTGAFDPDWPAC (SEQ ID) NO: 2), WENWMMMGNA (SEQ ID NO: 3), WENWMMGNAC (SEQ ID NO. 4) that induce an immunoprotective response against Group B Streptococci.

3. The peptide of claim 1, wherein the peptide is conjugated to a carrier.

4. A peptide having a sequence selected from the group consisting of FDTGAFDPDWPA (SEQ ID NO: 1), FDTGAFDPDWPAC (SEQ ID NO: 2), WENWMMMGNA (SEQ ID NO: 3), WENWMMGNAC (SEQ ID NO. 4) that induce an immunoprotective response against Group B Strep.

5. The peptide of claim 1, wherein the peptide specifically binds to multiple antibodies that specifically bind to Group B Streptococci Type III capsular polysaccharide.

6. The peptide of claim 5, wherein at least one of said multiple antibodies is antibody S9.

7. The peptide of claim 5, wherein said multiple antibodies are selected from the group consisting of polyclonal and monoclonal antibodies.

8. The peptide of claim 5 having a sequence selected from the group consisting of FDTGAFDPDWPA (SEQ ID NO: 1), FDTGAFDPDWPAC (SEQ ID NO: 2), WENWMMMGNA (SEQ ID NO: 3), WENWMMGNAC (SEQ ID NO. 4) that induce an immunoprotective response against Group B Streptococci.

9. The peptide of claim 5, wherein the peptide is conjugated to a carrier.

10. A peptide that induces an immunoprotective response against Group B Streptococci Type III capsular polysaccharide, the peptide being produced by the process of:

(a) contacting a phage peptide display library with one or more protective antibodies that specifically bind to a Group B Streptococci Type III capsular polysaccharide;

(b) isolating one or more phage from the phage peptide display library that bind to said one or more protective antibodies; and (c) identifying those peptides from the phage peptide display library that specifically bind to said one or more protective antibodies.

11. The peptide of claim 10, wherein one of said one or more protective antibodies is S9.

12. The peptide of claim 10, wherein said phage peptide display library is a nonapeptide library.

13. The peptide of claim 10 having a sequence selected from the group consisting of FDTGAFDPDWPA (SEQ ID NO: 1), FDTGAFDPDWPAC (SEQ ID NO: 2), WENWMMMGNA (SEQ ID NO: 3), WENWMMGNAC (SEQ ID NO. 4) that induce an immunoprotective response against Group B Streptococci.

* * * * *